United States Patent [19]
Wilhelm et al.

[11] Patent Number: 5,376,280
[45] Date of Patent: Dec. 27, 1994

[54] FLOCCULATION CONTROL SYSTEM AND METHOD

[75] Inventors: James H. Wilhelm, Sandy; C. J. H. Brest Vankempen, Salt Lake City; Ralph A. Cutler, Centerville; Vincent E. Hamilton, Salt Lake City, all of Utah

[73] Assignee: Westech Engineering, Inc., Salt Lake City, Utah

[21] Appl. No.: 143,495

[22] Filed: Oct. 25, 1993

[51] Int. Cl.$^5$ .......................... C02F 1/56; B01D 21/30
[52] U.S. Cl. ..................................... 210/741; 210/143; 210/207; 73/61.67; 73/61.71; 73/61.78; 364/502; 364/558; 364/571.02
[58] Field of Search ............... 73/61.67, 61.71, 61.78; 210/739, 740, 741, 744, 143, 198.1, 207; 364/500, 502, 558, 571.02

[56] References Cited

U.S. PATENT DOCUMENTS

| | | | |
|---|---|---|---|
| 3,723,712 | 3/1973 | Komline, Sr. et al. | 73/61.71 |
| 3,896,660 | 7/1975 | Valentyik | 73/61.67 |
| 4,140,007 | 2/1979 | Bosland et al. | 73/61.67 |
| 4,287,757 | 9/1981 | Bucsky et al. | 73/61.67 |
| 4,783,269 | 11/1988 | Baba et al. | 210/143 |
| 4,794,789 | 1/1989 | Natako | 73/61.67 |
| 4,855,061 | 8/1989 | Martin | 210/143 |
| 5,003,814 | 4/1991 | Crawford et al. | 73/61.71 |
| 5,037,559 | 8/1991 | Schmitt | 210/709 |
| 5,147,556 | 9/1992 | Taylor | 210/207 |
| 5,202,016 | 4/1993 | Church et al. | 210/85 |
| 5,240,594 | 8/1993 | Ho | 210/96.1 |

Primary Examiner—Neil McCarthy
Attorney, Agent, or Firm—Thorpe North & Western

[57] ABSTRACT

A flocculation control system for controlling a feed rate of a flocculant into an aqueous slurry comprises an elongate settling tube having an open lower end for placing into the slurry. An air eductor creates a subatmospheric pressure within the settling tube to thereby draw a sample of the slurry therein to a predetermined location above the slurry level. A control valve hermetically seals an upper end of the settling tube to maintain the subatmospheric pressure therein such that the sample is retained in a quiescent state and in fluid communication with the slurry body. A pressure sensor senses the subatmospheric pressure within the settling tube, and measurements thereof are taken at selectable intervals to develop an initial measurement of said pressure and intermediate lower magnitude measurements of said pressure resulting from the settling of particles from the sample. The pressure measurements enable calculation of the weight concentration and settling velocity of said suspended particulates. A desired settling velocity for optimizing flocculant feed rate can be determined from the weight concentration of the suspended particles. The feed rate of the flocculant is increased if the measured settling velocity is lower than a desired rate and decreased if the measured settling velocity is higher than a desired rate.

39 Claims, 2 Drawing Sheets

FLOCCULATION CONTROL SYSTEM AND METHOD

BACKGROUND OF THE INVENTION

1. The Field of the Invention

The present invention relates generally to a system for measuring the weight concentration and settling rate of suspended particles within an aqueous mediums. Mere particularly, it concerns a device and accompanying method for monitoring and/or controlling the feed rate of a flocculating agent into an aqueous slurry based upon the concentration and settling velocity of suspended particles within said aqueous slurry.

2. The Background Art

Aqueous slurry includes, but is not limited to, such diverse compositions as sewage sludge in sewage, industrial waste, fly ash, cellulosic paper pulp suspended in paper mill refuse fluid, biological sludges, fuel coal slurries, and metallurgical slurries. Such slurries comprise an aqueous mixture and suspension of finely divided particulate solids, some of which are hydrated and/or electrostatically charged.

In the interest of environmental protection and economic material handling, particulate solids suspended in aqueous slurries must be separated from the aqueous medium, or dewatered, prior to recycle or release of the fluid. As used herein, the term "dewater" refers generally to the separation of a liquid phase from a liquid phase/solid phase composition. The use of this term herein does not imply that the liquid separated is water, although in many instances this is in fact the case.

Traditional methods of separating suspended solids from an aqueous slurry are ineffective for the high volume demands of modern society. Conventional mechanical filtering and screening is incapable of economically separating many suspended solids from aqueous media. The reasons for this range from the hydrated nature of the solids to the fact that the particle size of the solids is often extremely small. A large percentage of suspended particles would dewater gravimetrically over time; however, this process is much too slow to meet the high volume demands of most processing facilities. In order for traditional gravimetric sedimentation to be effective, processing facilities would be required to build exceptionally large and expensive settling tanks and related equipment. Thus, alternative devices and methods have been researched and developed for accelerating the dewatering of aqueous slurry.

It is well known to separate suspended solids from an aqueous slurry by a process known as flocculation. Flocculation is a process by which finely divided particles suspended in an aqueous slurry are caused to agglomerate together to form relatively larger particles, or flocs. These larger particles can then be removed from the aqueous medium by any one or more of a number of physical separation processes such as filtration, sedimentation, and so forth. The process of flocculation involves the addition of a suitable flocculating agent, or flocculant, into the aqueous medium and agitating the slurry to thereby cause the agglomeration previously mentioned.

Flocculants refer to agents which favorably influence flocculation and/or the size, stability and dewaterability of the flocs formed. These include so-called "true flocculants" which cause flocculation of dissolved or colloidal constituents, and "flocculation aids," which favor agglomeration and solidification of the flocs. Common examples of flocculants include chemicals such as ferric chloride, calcium chloride, sulfuric acid, starch, lime, alum and synthetic polymers of an anionic, cationic or nonionic charge nature.

Flocculants are chosen according to the nature and quality of the aqueously suspended particles, which often are similarly charged such that they mutually repel one another. When a flocculant is added to such an aqueous medium it has the effect of attracting the particles with an opposite charge and/or neutralizing the charge of said particles, whereby the agglomeration of the particles is no longer inhibited by the mutual repulsion which previously retained the particles in a separated state. With the repelling forces removed, the particles agglomerate. The agglomeration greatly accelerates the settling of the particles since, in accordance with Stoke's Law, larger particles settle faster than smaller particles. The particles can be thereby quickly settled by gravity or separated by a mechanical screening device such as belt filter presses, and the resulting effluent is discharged to receiving waters. Flocculation is thus used to dewater various dispersions of aqueous sludge or slurry.

The success of dewatering by flocculation relies heavily upon accurate control over the amount of flocculant added to the fluid. If not enough flocculant is added, the charge neutralization of the suspended solids is incomplete. On the other hand, the addition of too much flocculant will cause excessive operating cost and may reverse the charges on the particles to thereby cause the same fine particle division in the treated medium as in the original untreated medium. Moreover, too much flocculant may also further contaminate the fluid. Modern concerns over environmental pollution and the cost of flocculant and other materials useful in preventing or minimizing such pollution have made it highly desirable to produce flocculants which cause higher degrees of separation at lower dosage levels.

Flocculants are expensive chemicals by most standards, and represent one of the most significant costs of plant operation. However, the feed rate of flocculant into aqueous slurry is seldom a constant or a fixed function of the slurry volume throughput (i.e. the amount of solids removed from the aqueous medium). Many factors variable to the slurry constituency continuously alter the flocculant demand. Consequently, operators must constantly evaluate and manually adjust the flocculant feed rate. For example, when a belt filter press is used, operators examine the consistency of the resulting sludge cake. A fluidized sludge cake upon filter press entry signifies insufficient flocculant, while a stiff and crumbling sludge cake suggests an excess of flocculant, and hence, waste. Because it is not always possible for plant operators to devote their full attention to the flocculant feed rate, operators have a natural tendency to overdose the slurry with flocculant. The need thus arose for accurate and consistent monitoring of flocculation.

The traditional method of monitoring and controlling the flocculant feed rate was to test a number of samples of the untreated slurry with different amounts of the flocculant. A flocculant concentration corresponding to optimum flocculation in the samples was obtained, and an equivalent concentration was used in the full-scale flocculating process. This process was laborious, time consuming, and inaccurate when applied to variable fluid flow and/or variable particulate concentration.

Numerous other methods have been used to monitor and control the flocculant feed rate, such as a simple sedimentation test, or the use of a test apparatus having a tubular mixing section and a turbidimeter which is calibrated for the conditioning plant where it would be used. These methods also failed to prove consistently accurate where the fluid flow and/or the particulate concentration varied over time.

Among the attempts to achieve accurate and consistent monitoring of flocculation are systems disclosed in U.S. Pat. No. 5,202,016 (which discloses a detection apparatus for monitoring the charge condition of suspended solids within an aqueous slurry and adjusting the flocculant feed rate accordingly) and U.S. Pat. No. 5,240,594 (which teaches using photodetectors to view the surface of an aqueous slurry, correlating a resulting output signal to a dryness value [i.e., a liquid/solid weight ratio for said slurry] and adjusting the flocculant feed rate accordingly). However the charge condition and the optical characteristics of aqueously suspended solids are poor indicators of the weight concentration of said solids within the aqueous medium. The weight concentration of the solids is directly pertinent to the settling velocity of the solids, and a knowledge of these parameters is needed, especially for optimizing flocculation processes dependent upon such settling velocity. Moreover, many of the prior art devices and methods monitor the characteristics of the suspended particles in the original, untreated aqueous medium and thus depend more upon theoretical and less upon the actual flocculation of the particles in controlling the flocculant feed rate.

There is thus a need for apparatus and methods for monitoring and controlling the flocculation feed rate of a dewatering process which is based upon a quick and accurate measurement of the concentration and settling velocity of treated suspended particles. There is further a need for such an apparatus which is consistently accurate when the fluid flow, particle size, surface charge, flocculation characteristics and/or the particulate concentration varies over time.

OBJECTS AND SUMMARY OF THE INVENTION

It is an object of the present invention to provide a system for measuring/monitoring the weight concentration and settling rate of suspended particles within an aqueous medium.

It is another object of the invention to provide such a system which only uses successive subatmospheric pressure readings, and nothing more, to measure the weight concentration and settling rate of suspended particles within an aqueous medium.

It is also an object of the invention to provide such a system for monitoring and controlling a process of adding flocculants to assist in separating the suspended particles from the aqueous medium, particularly when the process depends upon variable conditions such as the feed rate of a flocculant.

It is another object of the invention to provide such a system which analyzes a sample of aqueous slurry having flocculated particles therein while preventing shearing of said flocculated particles.

It is an additional object of the invention to provide such a system which noninvasively analyzes a sample of aqueous slurry and thus does not depend upon clarity of a sampling tube, placement of a probe, and so forth.

It is also an object of the invention to provide such a system which minimizes floc building and/or floc plugging within the system.

It is a further object of the invention to provide such a system which is easy to operate, accurate, and consistent, even if the flow rate of the aqueous medium, particle size, flocculation characteristics, surface charge and/or the particulate concentration varies over time.

It is also an object of the invention to provide such a system which optimizes flocculant consumption.

It is still another object of the invention to provide such a system which maximizes the slurry volume throughput of a liquid/solid separation process.

The above objects and others not specifically recited are realized in a specific illustrative embodiment of a measuring system which includes a settling tube having an open lower end for placing in fluid communication with a body of aqueous slurry contained in a feedwell, an air eductor coupled to an upper end of the settling tube for developing a subatmospheric pressure within the settling tube to thereby draw a sample of the slurry up into said settling tube to a predetermined level therein, and a sensor for sensing the level of the sample within the settling tube. A control valve disposed in the settling tube is responsive to the sensor for hermetically sealing the upper end of the settling tube from the air eductor when the sample has reached a predetermined level therein. A subatmospheric pressure is thereby maintained within the settling tube and retains the sample therein in a quiescent state and in fluid communication with the body of slurry. Suspended particles drop from the settling tube under gravity, thereby decreasing the weight of the sample and thus the subatmospheric pressure required to retain the sample. A pressure sensor is coupled to the settling tube below the control valve to provide multiple readings of the subatmospheric pressure. A controller calculates the weight concentration and settling velocity of the suspended particles within the sample from the known height of the sample above the slurry level, from the initial subatmospheric pressure when the sample is at its heaviest, and from the rate of change of the subatmospheric pressure as the particles drop from the tube. If the weight concentration and settling velocity indicate that agglomeration is taking place too slowly or too fast, i.e., too little or too much flocculant is being provided, the controller signals a pump to respectively increase or decrease its pumping rate of flocculant into the aqueous slurry. The optimal settling velocity for a particular slurry is user determined and can be discovered through successive lab tests to determine the settling characteristics and optimal settling velocities for a range of particle weight concentrations of the specific material to be flocculated. Once the range has been determined, this information can be incorporated into a computerized dosing program which allows for proper flocculant feed rate selection.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawing in which.

DETAILED DESCRIPTION

Figure 1:
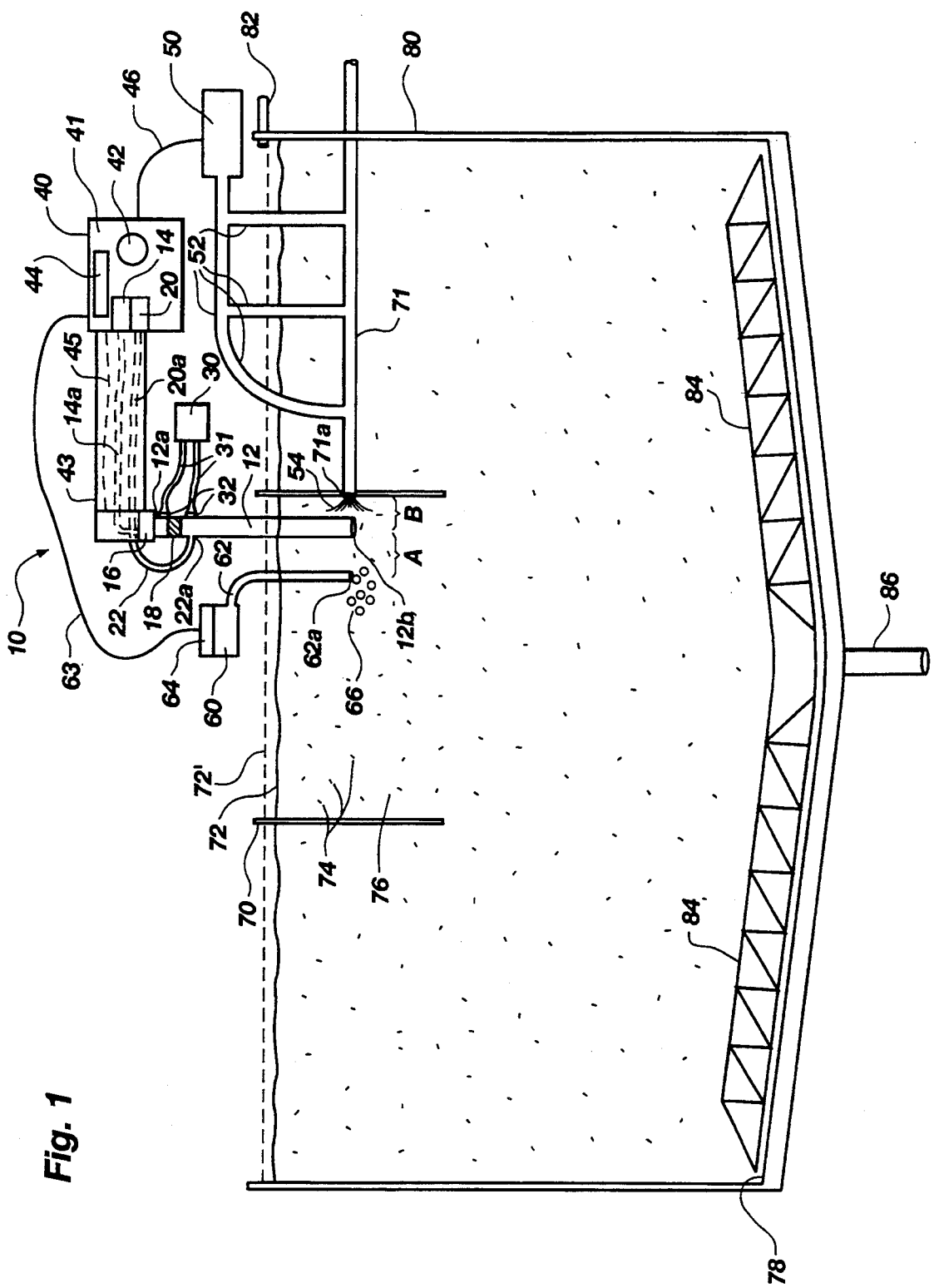
FIG. 1 is a side, schematic view of a flocculation control system made in accordance with the principles of the present invention.

A preferred embodiment in accordance with the present invention is illustrated schematically in FIG. 1 which shows a flocculation control system generally designated at 10. The system 10 includes a settling tube 12 having upper and lower ends 12a and 12b, respectively. Connected to said upper end 12a is a level probe 16 for sensing a fluid level within the settling tube 12 in a manner known to those skilled in the art. Also connected to said upper end 12a is a control valve 18 for hermetically sealing said upper end 12a, said control valve 18 preferably being a solenoid actuated, air operated valve. A rinse liquid source 30 includes rinsing tubes 31 fluidly connected to the settling tube 12 above and below the control valve 18. Valves 32 operate to open and close fluid communication between the rinse liquid source 30 and the settling tube 12.

The system 10 includes a controller having a control panel 41. The controller 40 includes an air eductor 14 a pressure sensor 20, a pressure gauge 42 responsive to pressure signals produced by the pressure sensor 20, and a display screen 44 for displaying to a user data collected and/or processed by the controller 40. The air eductor 14 and the pressure sensor 20 communicate with the settling tube 12 through a conduit 43, which is pneumatically and electrically connected to the upper end 12a of said settling tube. The controller is preferably powered by either a 120 volt power source, or a 220 volt power source.

The conduit 43 contains separate pneumatic connection tubes 14a and 20a for the air eductor 14 and the pressure sensor 20, respectively, and the necessary electrical connections 45 appurtenant thereto as known in the art. A pressure line 22 fluidly connects the pressure sensor pneumatics 20a within the conduit 43 with the settling tube 12 at a location 22a below the control valve 18. The pneumatic connection tubes 14a and 20a and the pressure line 22 are preferably capable of withstanding about 100 pounds per square inch (psi) and conveying fluid at a rate of approximately two cubic feet per minute (cfm). The electrical connections 45 also electrically connect the controller 40 to the level probe 16 and the control valve 18 in a manner known to those skilled in the art.

The level probe 16 is incorporated into the upper end 12a of the settling tube 12 and extends through a throat (not shown) of the control valve 18 to thereby sense the approach of liquid as known in the art. The level probe 16 may alternatively be mounted upon the controller 40 and extend electrically through the conduit 43 to a level sensor appropriately positioned within the settling tube 12.

The system 10 also includes an air supply 60 having a bubbling tube 62 and a pressure sensor 64. The pressure sensor 64 can be electronically connected to the controller by signal wire 63 to convey pressure data thereto, or remain independent thereof and display pressure data on a pressure gauge (not shown).

A signal wire 46 electrically connects the controller 40 to a polymer pump 50. Said polymer pump includes polymer injection pipes 52 which communicate with a slurry feed pipe 71. The polymer pump 50 pumps a polymer through the injection pipes 52 into the slurry feed pipe 71 to thereby induce flocculation within the slurry. Flocculating slurry 54 is in turn injected into a feedwell 70 at a feed pipe entry 71a.

The purpose and interrelationship of the elements identified above will be discussed in more detail below.

Figure 2:
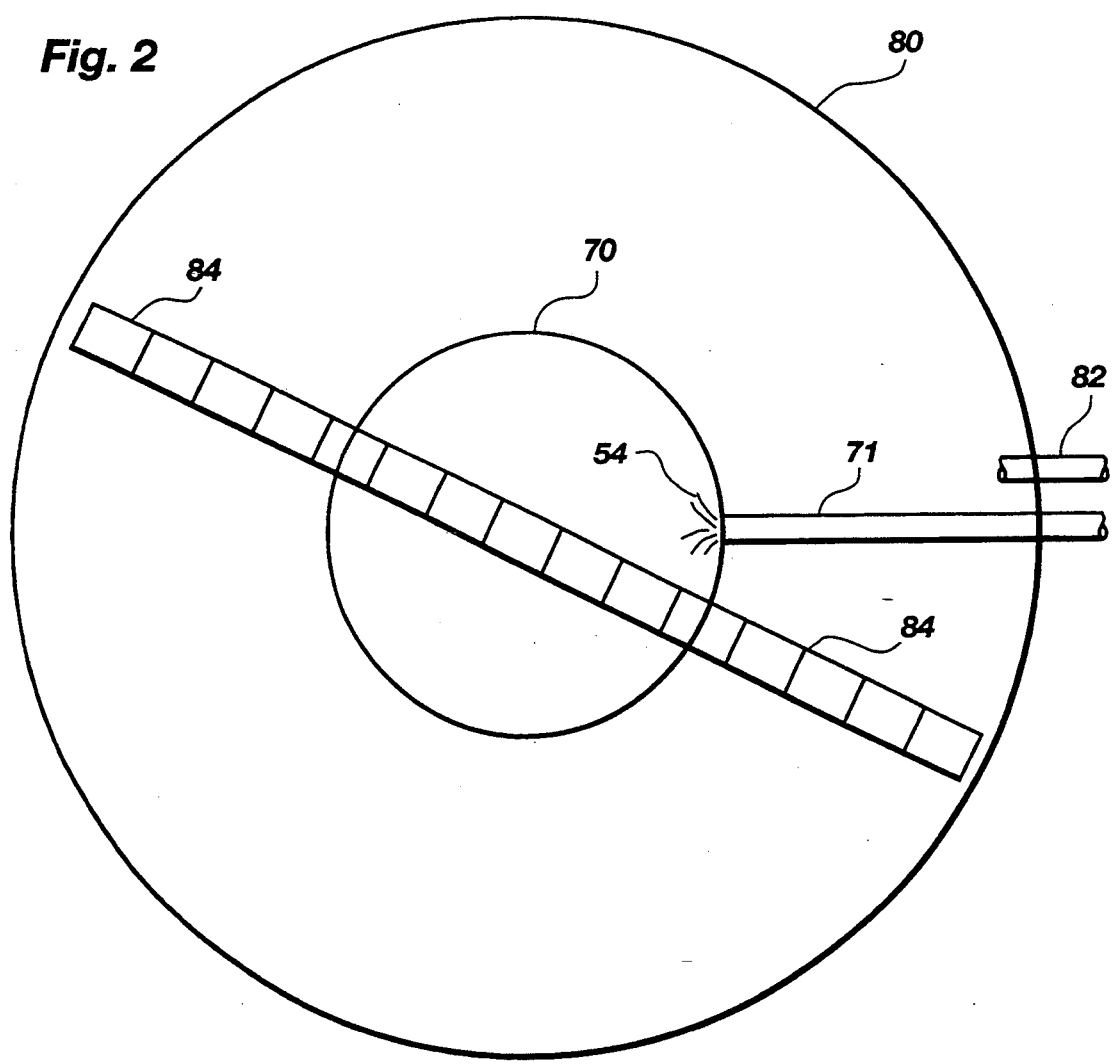
FIG. 2 is a plan view of the system of FIG. 1.

Reference is made to FIGS. 1-2. As is known in the art a feedwell as shown at 70 is generally located centrally within a thickener 80, which is a large holding tank through which a slurry flows. The thickener 80 includes an overflow outlet 82 and other structure which is not discussed herein. The slurry typically comprises solid particulates 74 suspended within an aqueous medium 76, and includes a slurry level 72. The thickener is generally constructed such that all of the slurry flows from the feed pipe 71 through the feedwell 70 and into the thickener 80.

The purpose of the feedwell 70 is, among other things, to dissipate kinetic energy in the flowing slurry and to feed said slurry into the thickener 80. Injecting polymer through injection pipes 52 into the feed pipe 71 insures that polymer is injected into substantially all portions of the slurry to thereby cause the particulates 74 to agglomerate into larger particles or flocs. The flocs gradually settle by force of gravity to the bottom of the thickener 80 to form a sludge cake 78. Other floc separation methods are employed in other systems in which the present invention can be used such as filtering, belt presses, and so forth. Rake arms 84 are activated to rake the sludge 78 out through an underflow outlet 86.

A principal concept in accordance with the present invention is subatmospheric pressure, or vacuum, as will now be explained conceptually. Unlike other flocculation control devices, the present invention takes the weight of the agglomerated flocs into account by using subatmospheric pressure to measure the weight concentration and settling velocity of the flocs. This is accomplished by using the air eductor 14 to develop subatmospheric pressure within the upper end 12a of the settling tube 12 to thereby draw a sample of slurry into said settling tube. The air eductor 14 is then hermetically sealed from the settling tube 12 by the valve 18, and the lower end of the tube 12b remains open. At this point, a subatmospheric pressure is maintained in the tube 12 which retains the sample in a quiescent state despite the lower end 12b of said tube remaining open.

This is illustrated by analogy to the common experience of a soda drinker drinking a glass of soda through a straw. The soda drinker develops subatmospheric pressure within the straw by sucking on the end of it. If the soda drinker places his or her tongue over the end of the straw while soda is being sucked therethrough, subatmospheric pressure is maintained within the straw to retain a sample of the soda therein. The soda is retained in the straw even though the lower end of the straw remains open and the soda sample resides above the level of the soda in the glass.

The subatmospheric pressure holding the slurry sample within the settling tube is measured by the pressure sensor 20 and compared with the subatmospheric pressure required to retain a liquid sample substantially free of particulates. Since most particulate solids are denser than water, the sample having particulates is heavier than the sample without and therefore requires more pressure to be retained. This difference in pressure is used to calculate the specific gravity and the concentration by weight of the suspended solids within the sample.

As time passes, the suspended particulates settle and fall through the open lower end 12b of the settling tube 12 by force of gravity, thereby decreasing the weight of the slurry sample and thus the subatmospheric pressure required to retain the sample. The pressure sensor 20 measures the resulting intermediate lower values of subatmospheric pressure at selectable intervals, and the rate of change in the subatmospheric pressure is calculated therefrom and used to calculate the settling velocity of the suspended particles. The pressure sensor 20 can alternatively be an electronic sensor which measures the decreasing pressure in a continuous fashion and sends an output signal proportional to the continuous pressure decrease to a computer which then calculates the rate of change in the subatmospheric pressure. The rate of change in the subatmospheric pressure, however, calculated, is used to calculate the settling velocity of the particles within the sample.

The weight concentration of the particulates 74 is a constant, whereas the settling velocity of said particulates and the feed rate of the polymer are variables. The invention varies the polymer feed rate responsive to the settling velocity to achieve a settling velocity within an optimal range for the existing weight concentration of particulates. If the measured settling velocity is not within the user defined optimal range, the feed rate of the polymer is increased or decreased until a desired settling rate for the existing weight concentration is achieved.

The features and method of a preferred embodiment in accordance with the present invention will now be explained in light of FIG. 1. The system 10 is positioned in a semi-permanent location at the feedwell 70, usually on a bridge (not shown). The lower end 12b of the settling tube 12 is preferably placed at a fixed position adjacent to the feed pipe entry 71a at a distance therefrom chosen by the user as designated by bracket B. Said lower end 12b may be placed anywhere below the slurry level 72. It is preferred that the settling tube 12 remain in the same position at all times and such that the upper end 12a resides at a location above the slurry level 72.

The system 10 is preferably calibrated by first taking a reference sample. The air eductor 14 is actuated to develop a subatmospheric pressure within the settling tube 12 to thereby draw a reference sample of the slurry through the open lower end 12b into said settling tube to the upper end 12a thereof and thus above the slurry level 72 within the feedwell 70. The level probe 16 senses when the reference sample reaches the upper end 12a. At this point, the control valve 18 closes to hermetically seal the air eductor 14 from the upper settling tube end 12a. This sealing action stops the flow of slurry into the settling tube 12 and maintains a subatmospheric pressure within said tube to thereby retain the reference sample in a quiescent state, with the lower end 12b remaining open and thus in fluid communication with the slurry in the feedwell. The air eductor 14 can be made responsive to the valve 18 to deactivate when said valve closes.

The reference sample is retained long enough for substantially all suspended particulates 74 to settle from the open lower end 12b of the settling tube 12 back into the feedwell 70 by force of gravity, usually for approximately twenty minutes. A reference pressure reading is then taken from the pressure sensor 20 of the subatmospheric pressure required to retain this particulate-free reference sample. This reference pressure reading is correlated to the height of the reference sample retained above the slurry level 72. Subsequent pressure readings are compared with said reference pressure reading, which correlates to the amount of the reference sample retained above the slurry level, as more fully explained below. It is noted that the pressure line 22 communicates with the settling tube 12 at a location 22a below the control valve 18, since the pressure readings are taken when the valve 18 is closed.

It is to be understood that calibration of the system 10, although preferred, is not necessary. For example, the known density of water could be used with the known volume within the settling tube 12 above the slurry level 72 to calculate the weight of a particulate-free sample of water for use as the reference pressure reading, although this method may prove less accurate than obtaining reference pressure from an actual reference sample.

After the reference sample of slurry has been taken and analyzed in the manner described, it is purged from the system 10 and a new sample is drawn into the settling tube 12 in the same manner. The pressure sensor 20 senses the initial subatmospheric pressure required to retain the sample. Since the volume of the sample above the slurry level 72 is substantially identical to that of the reference sample (assuming the slurry level 72 has not changed), the reference pressure reading can be subtracted from this initial pressure reading to obtain the pressure differential. The pressure differential is used to determine the weight of the suspended particulates 74 within the sample in a manner known to those skilled in the relevant mathematics. The pressure differential is also used to calculate the specific gravity of the particulates 74 and the concentration by weight of said particulates relative to the sample above the slurry level 72, preferably in units of pounds of particulate per gallon of liquid (lb./gal.). Changes in the slurry level 72 are taken into account mathematically, as will be discussed below.

As discussed above, with the sample retained within the settling tube 12 in a quiescent state, the suspended particulates 74 which are denser than the aqueous medium 76 settle and pass through the bottom 12b into the feedwell 70 by force of gravity. The pressure sensor 20 takes intermediate measurements of said pressure, which are progressively lower as a result of the settling of particles from the sample. The intermediate lower pressure readings are taken in known time intervals sufficient for use in calculating the settling velocity of the suspended particulates 74 in a manner known to those skilled in the relevant mathematics, preferably in units of inches per minute.

The controller 40 can be programmed as known in the art to enable a user to select the length of said time intervals, and to automatically select a "default" time interval if the user fails to do so. It will be appreciated that a separate calculation of settling velocity can be made for each pressure reading, and that there will likely be some variation between each calculation. The system 10 will take as many pressure readings as are necessary until a consistent value for settling velocity is achieved.

The pressure gauge 42 is electrically connected to the pressure sensor 20 and provides a display of pressure readings to the user. The pressure sensor 20 is electronically connected to the controller 42 and sends signals thereto corresponding to the pressure readings, to enable said controller 42 to utilize computer means therein as known in the art for making calculations of weight concentration and settling velocity of the particulates 74 within the sample. The user may alternatively undertake to calculate the weight concentration and settling velocity from the pressure measurements displayed by the gauge 42 and from the known dimensions of the sample.

It will be appreciated that since the lower end 12b of the settling tube 12 is preferably located near the feed pipe entry 71a, the samples taken represent the slurry in its treated state. This represents greater empirical significance when comparing the system 10 to some prior art devices which only analyze untreated samples of the slurry. Analysis of untreated samples of slurry results in mere predictions of particulate behavior upon variation of the polymer feed rate, whereas analysis of treated samples results in measurements of the actual behavior of the particulates after variation of the polymer feed rate.

It is preferred that the settling tube 12 have a constant diameter and be positioned to extend substantially vertically into the slurry. However, the settling tube 12 may alternatively extend into the aqueous medium at an inclined position to thereby increase the settling velocity of the particles within the sample and enable shorter intervals between pressure measurements.

The controller 40 includes computer means (not shown) as known in the art to achieve at least the following particulars. The controller 40 is programmably arranged to receive the parameters and readings discussed and thereby make the calculations mentioned, preferably by means of a microprocessor. The controller 40 is operable by a user to store and retrieve data for display on the display screen 44 including pressure measurements, settling velocities, weight concentrations, and polymer feed rates. The current measured data, correlations and calculations are also viewable by the display screen 44.

The system 10 is thus useful for determining the weight concentration and settling velocity of suspended particles within an aqueous slurry. An important use of these values is in determining an optimal, "target" settling velocity corresponding to an optimal polymer feed rate for a particular slurry. A user may determine an optimal settling velocity in any manner desired. For example, an optimal settling velocity may be viewed as a function of the particle concentration in the slurry. An optimal settling velocity may also be determined by the user without regard to the weight concentration of the particles within the aqueous slurry. It is consistent with an aspect of the present invention to allow the user to use the measurements of settling velocity and weight concentration in any manner desired.

The system 10 may be advantageously used in either manual control or automatic control modes. The controller 40 is operable by a user for selecting between these two modes. If the user determines some mathematical relationships between settling velocity, particle concentration and flocculant feed rate for the specific slurry, these relationships may be incorporated into a computerized dosing program which allows for selection of any desired degree of flocculation and concomitant automatic control of flocculant pumping to maintain a selected degree of flocculation.

When automatic control is selected, the system 10 is responsive to the calculations of the controller 40 to automatically adjust the feed rate of the polymer via the signal wire 46 either up or down, depending on the optimal settling velocity specified for the particulates 74. For example, the user may determine an optimal settling velocity of about twenty inches per minute for a copper weight concentration equal to five percent. If the actual settling velocity is measured at seven inches per minute, the controller 40 will send a signal through the signal wire 46 to the polymer pump 50 to increase the polymer feed rate until the optimal settling velocity of twenty inches per minute is achieved, or until the settling velocity reaches some optimal range encompassing the optimal rate of twenty inches per minute. Computer structure and process for varying a pump responsive to an electronic signal in the manner described are known to those having ordinary skill in the art.

Alternatively, a particular user may desire to utilize the system 10 in a strictly monitoring capacity and make manual adjustments to the polymer feed rate. The user would operate the controller 40 to select manual mode, and would observe the calculation of feed concentration and settling velocity by viewing the display screen 44. The user will develop an intuitive feel for selectively increasing or decreasing the polymer feed rate until the desired settling velocity is achieved. This practice is often useful to train the user in the workings of flocculation control. The user may also use his or her visual observations of the supernatant clarity of the slurry and the level and density of the sludge cake 78 in determining by how much to vary the polymer feed rate.

It will thus be appreciated that the polymer feed rate may be adjusted automatically by the controller 40, or by a human being. It will also be appreciated that, instead of a computer calculating the settling velocity and weight concentration of the suspended particles 74, a human being may use the pressure measurements and known sample dimensions to make these calculations.

The system 10 is rinsed and purged between samples, preferably in the following manner. After a sample has been analyzed, the valve 18 is opened to allow the sample to drain back into the feedwell 70. Valves 32 are opened to allow the liquid source 30 to inject water into the settling tube 12 above and below the valve 18 via rinsing tubes 31. The rinsing tubes 31 are preferably capable of operating under a pressure range of about 40–80 pounds per square inch (psi). The settling tube 12 is thereby thoroughly rinsed out to inhibit accumulation of solids, after which valves 32 and control valve 18 are closed. Air is then forced through the pressure line 22 at a preferred pressure of about three pounds per square inch (psi) in any manner known in the art to thereby force air through the settling tube 12 a and out the lower end 12b thereof to purge any remaining matter from said settling tube. The control valve 18 is then opened and the air eductor 14 is actuated to draw a new sample, and the cycle is repeated.

The various steps accomplished by the present invention may be modified and/or alternatively arranged in any manner which will fulfill any objects or advantages of the present invention. All such steps, including the drawing of the sample, the operation of the control valve 18, and the operation of the rinse cycle can be programmably arranged to be activated automatically by a computer. Alternatively and as previously discussed, manual control of all such steps is also within the scope of the present invention. For example, electronic actuating buttons may be placed on the controller 40 or elsewhere for manual control of the steps.

Another significant feature of a preferred embodiment of the present invention is a calibration option accomplished by provision of the air supply 60. Those having experience in the pertinent field will appreciate that the slurry level 72 in the feedwell 70 varies. It will also be appreciated that each time the slurry level 72 changes to a new level 72', the data collected from the reference sample are thereby rendered ineffective, since the amount of sample retained above the liquid level will also necessarily change. Taking and analyzing a new reference sample each time the slurry level 72 changes would be laborious and time consuming.

Accordingly, the system 10 may be calibrated in the following manner. A reference air pressure reading is taken by pressure sensor 64 concurrently with the reference sample. This is done by operating the air supply 60 in the manner known in the art such that just enough air pressure is supplied to bubbling tube 62 to force a bubble of air 66 into the slurry. The bubbling tube 62 includes a distal end 62a which is preferably positioned in a fixed location adjacent to the lower end 12b of the settling tube 12 at a distance therefrom illustrated by bracket A, preferably six inches. The pressure required to force air into the slurry (hereinafter "purge pressure") is recorded manually or may be conveyed electronically to the controller 40.

When the slurry level 72 significantly changes to a new level as in level 72', the amount of sample retained above the slurry level changes and the air supply 60 can be actuated to take a new purge pressure reading. This new reading varies in direct proportion to the submersion depth of the settling tube 12, i.e. it will be greater than the initial reading if the slurry level 72 has increased, and less if said slurry level has decreased. The reference subatmospheric pressure reading, which is inversely proportional to the immersion depth of the settling tube 12, is then adjusted accordingly in a manner known to those skilled in the relevant mathematics to equal the pressure required to retain a particulate-free sample equal in volume to the sample retained above the new slurry level 72', and subsequent samples are compared against this adjusted subatmospheric pressure reading. The air supply 60 thus allows for adjusting the reference subatmospheric pressure inversely proportionally with the submersion depth of the settling tube 12 in a manner known to those skilled in the relevant mathematics to allow for accurate determinations of particulate concentration, and hence settling velocity, in subsequent samples. This feature avoids the need to analyze a new reference sample each time the slurry level 72 changes, any can be developed to be actuated automatically or manually.

It will be appreciated that the variation in the slurry level 72 can be compensated for in many different ways, all of which are within the scope of the present invention. For example, instead of a separate bubbling tube 62, purge pressure readings can be taken of the air purged through the settling tube during the rinse cycle. Another alternative includes arranging the settling tube 12 to be secured in the lateral direction, slidably disposed in the vertical direction and placed on a floatation device such that said tube rises and drops with changes in the slurry level 72. In this manner, the amount of sample drawn above the slurry level 72 would also be the same, and no compensation adjustments would need to be made to the data obtained from the reference sample.

The floatation alternative to the air supply 60 could be further enhanced by a telescopically adjustable settling tube with the lower end 12b in a fixed position. For example, if the slurry level 72 increases, the resulting rise of the floatation device would telescopically increase the length of the settling tube to raise the upper end 12a while the lower end 12b would remain the preferred distance from the feed pipe entry 71a. Similarly, the length of the settling tube would telescopically decrease with decreases in the slurry level 72. The sample would thereby always be drawn consistently from the same location relative to the feed pipe 71a, and the amount of sample drawn above the slurry level 72 would always be the same, so that the reference data taken from the reference sample would always be valid.

Still another significant feature in accordance with an aspect of the present invention allows for correction for settling which occurs while the sample is being drawn into tube 12. The time required to fill can be recorded and multiplied by the last known value of settling velocity, or some estimation of settling velocity. This yields mathematically the theoretical quantity of particle-free sample resulting from the settling of particles during drawing of the sample into the settling tube 12. From this theoretical quantity can be calculated a corrected value of settling velocity, and a corrected value of weight concentration, as discoverable by those skilled in the relevant mathematics.

Figure 3:
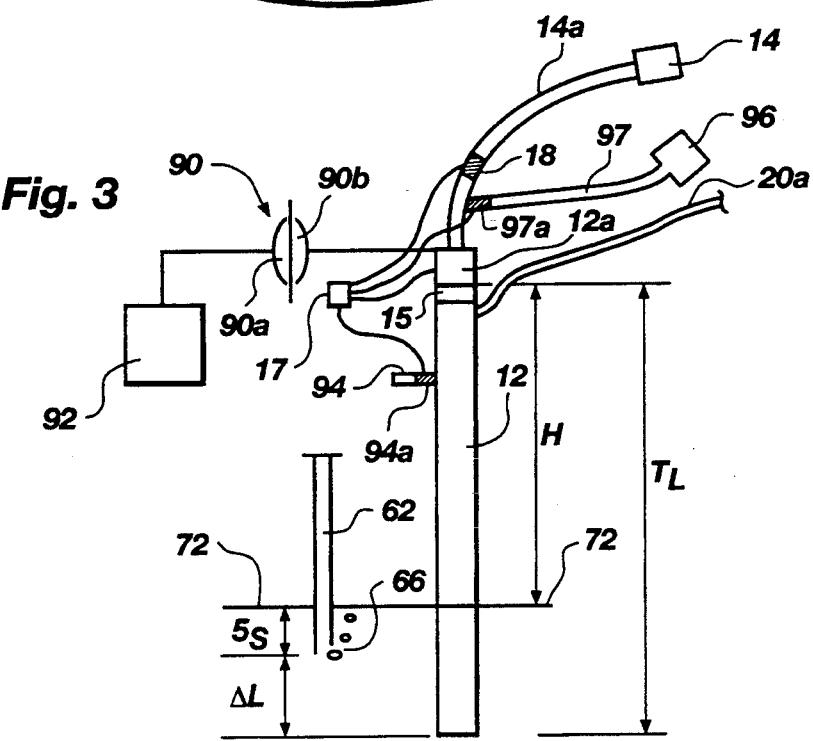
FIG. 3 is a side, schematic view of an alternative embodiment of the system of FIG. 1.

Another preferred embodiment of the present invention is depicted schematically in FIG. 3. The control valve 18 is disposed in the air eductor pneumatic connection tube 14a which is fluidly connected to the upper end 12a of the settling tube 12. An alternative to the level probe 16 of FIG. 1 is accomplished as follows. Assume that either the tube 12 is electrically conductive, or alternatively that the inner surface of the tube 12 is lined with electrically conductive material, except that said inner surface includes a band 15 of non-conductive material. It will be appreciated that a sensing device 17 can be electrically connected to the valve 18 and the conductive upper end 12a above the non-conductive band 15 for electrically sensing the presence and absence of the sample against said conductive upper end 12a. The valve 18 can be made responsive to the sensing device 17 such that as the slurry sample is drawn into the tube 12, the valve 18 closes to thereby hermetically seal the air eductor 14 from the tube 12 upon receiving a signal from the sensing device 17 signaling that the sample has reached the top of the non-conductive band 15.

This level-sensing feature can be combined with an air source 96 fluidly connected to the pneumatic connection tube 14a at a location below the control valve 18 by an air introducing tube 97. It will be appreciated that the practicalities of filling the tube 12 are such that by the time the valve 18 seals off the air eductor 14 from the tube 12, the level of the sample actually ends up somewhere above the non-conductive band 15. The air source 9 can be activated to slowly introduce air into the pneumatic connection tube 14a to thereby lower the upper level of the sample. When the sensing device 17 senses that the sample has fallen below the conductive upper end 12a, at activates a valve 97a to close off the air introducing tube 97 from the pneumatic connection tube 14a such that the upper surface level of the sample is consistent from one use to the next.

In the alternative, the level-sensing feature can be combined with a sample draw-off tube 94 which is fluidly connected to the tube 12. After the settling tube 12 has been filled, the tube 94 can then be activated to slowly draw off a portion of the sample to thereby lower the upper level of said sample. When the sensing device 17 senses that the sample has fallen below the conductive upper end 12a, it activates a hose valve 94a to close off the hose 94 from the tube 12 such that the upper surface level of the sample is consistent from one use to the next.

Referring still to FIG. 3, it will be appreciated that a differential pressure transducer 90 can be used to make the pressure measurements within the settling tube 12. The transducer 90 includes a diaphragm 90 having first and second ports 90a and 90b, respectively. The first port 90a is pneumatically connected to a reference vacuum source 92 for supplying a reference vacuum equal in magnitude to the subatmospheric pressure required to retain a column of substantially particle-free water of equal dimension to the sample retained within the settling tube 12. The second port 90b is pneumatically connected to the upper end 12a of the settling tube 12. The transducer 90 operates as known in the art to measure the difference between the subatmospheric pressure within the settling tube 12 and the reference vacuum. The rate of change of the pressure within the settling tube 12 resulting from the settling of particles can be calculated from the pressure differential measurements over time, or can be measured directly by the transducer 90, depending on the type of transducer used. The settling velocity is calculated from the rate of the pressure change. An advantage of the differential pressure transducer 90 is that it improves the accuracy of the pressure measurements. It will be appreciated that a non-differential pressure transducer can alternatively be used to measure the pressure within the settling tube 12 relative to the atmospheric pressure to thereby calculate settling velocity.

FIG. 3 also illustrates the relevant mathematical relationships involved in calculating the specific gravity of the slurry, and it will be appreciated that since the tube 12 is of a constant diameter, one need not compute the volume of the sample retained within the tube in order to solve for the specific gravity of the slurry. The symbol $T_L$ represents the length of the settling tube 12. The symbol H represents the height of the sample above the slurry level 72, which is the height of the sample retained within the tube 12 by the subatmospheric pressure. The symbol $S_S$ represents the submersion depth of the bubbling tube 62. The symbol $\blacktriangle L$ represents the difference in submersion depth between the bubbling tube 62 and the settling tube 12. Therefore, $$H = T_L - \blacktriangle L - S_S. \tag{1}$$

In addition, for a slurry comprised of a liquid having suspended particulates therein, and where the symbol SG represents specific gravity, $$\text{Reference Vacuum} = (H)(SG_{Liquid}); \tag{2}$$

$$\text{Pressure Differential} = (H)(SG_{Slurry} - SG_{Liquid}). \tag{3}$$

It can be seen from equation (3) above that by using the differential pressure transducer 90 to measure the pressure differential described above, one may use the known value of H to solve for $SG_{Slurry}$, which can be used to calculate the weight concentration of the solids in the slurry. It will be appreciated that a user need not use the volume V of the sample above the slurry level 72 to solve for specific gravity of solids given the constant diameter of the tube 12. However, said volume V may be incorporated into the above equations if desired.

Those skilled in the art will appreciate that the scope of the present invention encompasses many combinations and a broad spectrum of features and structures equivalent to those specifically discussed herein. For example, a subatmospheric pressure may be created within the settling tube 12 by any source of subatmospheric pressure known in the art, such as a vacuum pump or other suction means. It is presently preferred to use an air eductor 14 for this purpose.

A pinch valve is preferred for use as the control valve 18, but any valve means may be used therefore. Any level sensing means may be used alternatively to the level probe 16. Although the level probe 16 is used to sense the occurrence of the sample reaching a predetermined level, other sensing means capable of sensing a plurality of levels may be used. The invention is useful to monitor any type of suspended particulates within any type of aqueous medium, and may be used in conjunction with any type of flocculating device which injects flocculant into an aqueous medium.

The invention may be used to monitor and control the feed rate of any kind of flocculant, for example ferric chloride, calcium chloride, sulfuric acid, starch, lime, alum, synthetic polymers of an anionic, cationic or nonionic charge nature, or any other kind of polymer.

It is preferred that the settling tube 12 comprise a CPVC tube (corrosion resistant plastic pipe), because CPVC is chemically inert and therefore will not rust or corrode. However, any kind of material or tube type may be used, such as stainless steel pipe, painted mild steel, copper, conventional PVC, acrylic and so forth.

The preferred geometry of the settling tube 12 includes a settling tube having a constant diameter of approximately two inches. This geometry is preferably combined with a slow draw by the air eductor 14 of the slurry into the settling tube 12 (preferably at a draw rate of less than two feet per second) to thereby avoid shearing the flocs apart as they enter the tube. As discussed, the flocs are simply agglomerations of separate particles which, if quickly forced into a small tube, will shear, or break apart upon entry into the settling tube. Floc shearing would result in inaccurate determinations of settling velocity and must therefore be avoided. It is noted that the system 10 only draws slurry samples into a uniform settling tube 12 of constant diametric dimension, as opposed to many prior art devices which draw the sample through an orifice or constricted tube before said sample arrives in the settling chamber. The system 10 therefore provides superior operating capacity compared to the prior art devices in that floc shearing is minimized and even avoided.

It is also noted that the settling tube 12 contains no obstructions, corners or other structure impeding the flow of slurry therein. Such impediments tend to entrap or otherwise collect flocs and thereby produce bothersome plugging, buildup and so forth which requires additional time, effort and expense to clean. The configuration of the present invention thus has the advantage of minimizing floc buildup within the settling tube 12 as compared to prior art devices which fail to utilize a uniform tubular analysis chamber substantially free of obstructions.

Those skilled in the art will also appreciate additional environments in which the invention can be used. For example, the system 10 need not be confined to a feedwell, but can be useful in any liquid having suspended particles therein such as lakes, rivers and any process or waste fluid. While the present invention is described in terms of a flocculation control device, it is to be understood that the present invention is not limited thereto but may be useful in any application requiring the calculation of settling velocity of suspended particulates within an aqueous slurry. The present invention may also be useful in any application requiring the calculation of the specific gravity and weight concentration of the suspended particles within an aqueous slurry. The principles of the invention may thus be used in any setting requiring the advantages thereof. Those having ordinary skill in the field of this invention will appreciate the advantages of the invention, and its application to a wide variety of uses.

The present invention represents a significant advance in the field of flocculation monitoring and control. It is noted that many of the advantages of the present invention accrue due to the use of subatmospheric pressure to measure the weight concentration and settling velocity of particulates suspended in an aqueous medium. The problems associated with measuring only settling rate or using measuring chambers closed at the bottom are overcome to a significant degree by the present invention. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention. For example, appropriate valving could allow the rinse liquid source 30 and the pressure sensor 20 to utilize common tubing. The various features of the invention may be located and situated in many alternative arrangements, either directly on top of the settling tube 12, on the controller 40, or in some other arrangement. Numerous other modifications and arrangements not specifically mentioned herein are within the scope of the present invention, and the appended claims are intended to cover such modifications and arrangements.

What is claimed is:

1. A flocculation control system for monitoring and controlling the feed rate of a flocculant into an aqueous medium having suspended particles therein comprising:

hollow holding means for holding a column of the aqueous medium, said holding means having an upper end and an open lower end for placement into the aqueous medium;

means for developing a subatmospheric pressure within the upper end of the holding means to thereby draw a sample of the aqueous medium into said holding means through the open lower end thereof to a location above an upper surface of said aqueous medium to thereby retain the sample in a quiescent state such that suspended particles within the sample gradually drop through the open lower end of the holding means by force of gravity;

means for measuring the pressure over time within the holding means after the sample has been drawn thereinto to thereby develop a measurement of the rate of change of said pressure resulting from the settling of particles from the sample;

means for determining the height of the sample retained within the holding means above the upper surface of the aqueous medium;

means for calculating the settling velocity of the particles within the sample from the rate of change of the pressure within the holding means and from the height of the sample retained within the holding means above the upper surface of the aqueous medium and generating a signal corresponding to said settling velocity; and control means responsive to the signal for increasing the feed rate of the flocculant if the settling velocity is lower than a first value and for decreasing the feed rate if the settling velocity is higher than a second value, to thereby achieve a desired settling velocity of the suspended particles corresponding to an optimal flocculant feed rate.

2. A flocculation control system as in claim 1 wherein the means for measuring the pressure includes means for measuring the pressure at selectable intervals after the sample has been drawn thereinto to thereby develop an initial measurement of said pressure, and intermediate lower magnitude measurements of said pressure resulting from the settling of particles from the sample.

3. A flocculation control system as in claim 2 wherein the means for calculating the settling velocity further comprises:

means for calculating the weight concentration of the particles within the sample from at least one pressure measurement and the height of the sample retained within the holding means above the upper surface of the aqueous medium; and means for determining a desired settling velocity from the weight concentration of the particles within the sample.

4. A flocculation control system as in claim 3 wherein the weight concentration calculating means calculates the weight concentration of the suspended particles within a sample from an initial measurement of the pressure and a final measurement of the pressure.

5. A flocculation control system as in claim 1 wherein the settling velocity calculating means and the control means collectively comprise a computer electronically connected to the control means.

6. A flocculation control system as in claim 1 further comprising:

a pressure tube pneumatically connecting the subatmospheric pressure developing means to the upper end of the holding means;

means disposed on the upper end of the holding means for sensing the surface level of the sample therein; and valve means disposed within the pressure tube below the subatmospheric pressure developing means, said valve means being responsive to the surface level sensing means for hermetically sealing the subatmospheric pressure developing means from the upper end of the holding means when the sample has reached a level therein to thereby maintain a subatmospheric pressure within said holding means and retain the sample in a quiescent state therein.

7. A flocculation control system as in claim 6 wherein the surface level sensing means comprises a level probe disposed within the upper end of the holding means.

8. A flocculation control system as in claim 6 wherein the surface level sensing means comprises:
at least one electrically conductive portion of the holding means at the upper end thereof; and
means electrically connected to the valve means and the conductive portion for electrically sensing the presence and absence of the sample against said conductive portion to thereby signal the valve means when the sample has reached a predetermined level within the holding means.

9. A flocculation control system as in claim 8 further comprising at least one air-introducing tube pneumatically connected to the pressure tube at a location below the valve means for introducing air into the pressure tube to thereby lower an upper level of said sample to a location within the holding means.

10. A flocculation control system as in claim 8 further comprising at least one draw-off tube fluidly connected to the holding means at a location below the valve means for removing a portion of the sample from said holding means to thereby lower an upper level of said sample to a predetermined location within the holding means.

11. A flocculation control system as in claim 1 wherein the pressure measuring means comprises:
a differential pressure transducer having first and second ports, the first port being in pressure-sensitive contact with a reference subatmospheric pressure source for supplying a reference subatmospheric pressure to said first port, the second port being pneumatically connected to the upper end of the holding means, the transducer including means for measuring the pressure differential between the ports to thereby develop a measurement of the rate of change of said pressure resulting from the settling of particles from the sample.

12. A flocculation control system as in claim 11 wherein the reference subatmospheric pressure is equal in magnitude to the subatmospheric pressure required to retain a column of substantially particle-free water of equal dimension to the sample retained within the holding means.

13. A flocculation control system as in claim 11 wherein the holding means resides at a fixed position within the aqueous medium such that the immersion depth of the holding means therein, and the vacuum required to retain the sample within the holding means above the upper surface of the aqueous medium, vary with variation in the upper surface of said aqueous medium, the system further comprising:
means connected to the reference subatmospheric pressure source for varying the reference subatmospheric pressure substantially inversely with variation in the immersion depth of the holding means.

14. A flocculation control system as in claim 13 wherein the means for varying the reference subatmospheric pressure comprises:
an air pump for pumping air into the aqueous medium;
an air tube residing at a fixed position within the aqueous medium, said air tube being fluidly connected to the air pump for channeling the air pumped therefrom into the aqueous medium at a fixed location therein;
sensor means connected to the air pump for measuring the air pressure required to pump air into the aqueous medium, said air pressure varying directly with variation in the immersion depth of the holding means; and
means electronically connected to the sensor means and the reference subatmospheric pressure source and responsive to the gauge means for automatically varying the reference subatmospheric pressure inversely with variation in the air pressure required to pump air into the aqueous medium.

15. A flocculation control system as in claim 1 further comprising means pneumatically connected to the upper end of the holding means for driving air into said holding means to thereby pneumatically force the sample from the open lower end of said holding means.

16. A flocculation control system as in claim 3 further comprising computer means electronically connected to the pressure measuring means and the settling velocity calculating means for storing and retrieving data associated with samples drawn from the aqueous medium.

17. A flocculation control system as in claim 1 wherein the holding means comprises a hollow settling tube.

18. A flocculation control system as in claim 17 wherein the settling tube comprises a substantially straight tube having a substantially constant inner diameter.

19. A flocculation control system as in claim 3 wherein the control means further comprises:
a display screen electronically connected to the settling velocity calculating means and responsive thereto for displaying to a user representative numerical values of the weight concentration and settling velocity of the suspended particles within the sample to thereby enable said user to selectively manually vary the feed rate of the flocculant responsive to said numerical values; and
a selectively activatable signal wire electrically connecting the settling velocity calculating means to a flocculant pump for electrically conveying the signal to said flocculant pump to thereby cause said flocculant pump to increase the feed rate of the flocculant if the settling velocity is lower than a first value and to decrease the feed rate if the settling velocity is higher than a second value.

20. A flocculation control system as in claim 3 wherein the control means further comprises a display screen electronically connected to the settling velocity calculating means and responsive thereto for displaying to a user representative numerical values of the weight concentration and settling velocity of the suspended particles within the sample to thereby enable said user to selectively manually vary the feed rate of the flocculant responsive to said numerical values.

21. A flocculation control system as in claim 3 wherein the control means further comprises a selectively activatable signal wire electrically connecting the settling velocity calculating means to a flocculant pump for electrically conveying the signal to said flocculant pump to thereby cause said flocculant pump to increase the feed rate of the flocculant if the settling velocity is lower than a first predetermined value and to decrease the feed rate if the settling velocity is higher than a second value.

22. A flocculation control system as in claim 1 wherein the flocculant is a material selected from the group consisting of ferric chloride, calcium chloride, sulfuric acid, starch, lime, alum, anionic polymers, cationic polymers and nonionic polymers.

23. A flocculation control system as in claim 1 wherein the means for developing a subatmospheric pressure comprises an air actuated eductor pneumatically connected to the upper end of the holding means.

24. A flocculation control system as in claim 6 wherein the pressure measuring means further comprises:
  a pressure sensor pneumatically connected to the upper end of the holding means and thus below the valve means for sensing the pressure within said holding means; and
  a pressure gauge electrically connected to the pressure sensor and responsive thereto for conveying to the settling velocity calculating means a signal representing the pressure within the holding means.

25. A flocculation control system as in claim 3 wherein the means for determining the height of the sample further comprises means for determining the volume of the sample retained within the holding means above the upper surface of the aqueous medium, and wherein the settling velocity calculating means calculates the settling velocity and the weight concentration from said volume and from the pressure measurements.

26. A flocculation control system as in claim 1 wherein the aqueous medium comprises an aqueous slurry.

27. A flocculation control system as in claim 1 further comprising:
  a rinse liquid source fluidly connected to the holding means for rinsing an inner surface thereof to thereby inhibit accumulation of particles thereon.

28. A flocculation control system as in claim 6 further comprising:
  a rinse liquid source fluidly connected to the holding means and to the pressure tube at a location above the valve means for rinsing an inner surface of said holding means and pressure tube to thereby inhibit accumulation of particles thereon.

29. A system for measuring the settling rate of suspended particles within an aqueous medium comprising:
  hollow holding means for holding a column of the aqueous medium, said holding means having an upper end and an open lower end for placement into the aqueous medium;
  means for developing a subatmospheric pressure within the upper end of the holding means to thereby draw a sample of the aqueous medium into said holding means through the open lower end thereof to a location above an upper surface of said aqueous medium to thereby retain the sample in a quiescent state such that suspended particles within the sample gradually drop through the open lower end of the holding means by force of gravity;
  means for measuring the pressure over time within the holding means after the sample has been drawn thereinto to thereby develop a measurement of the rate of change of said pressure resulting from the settling of particles from the sample;
  means for determining the height of the sample retained within the holding means above the upper surface of the aqueous medium; and
  means for calculating the settling velocity of the particles within the sample from the rate of change of the pressure within the holding means and from the height of the sample retained within the holding means above the upper surface of the aqueous medium.

30. The system as in claim 29 further comprising:
  a pressure tube pneumatically connecting the subatmospheric pressure developing means to the upper end of the holding means;
  means disposed on the upper end of the holding means for sensing the surface level of the sample therein; and
  valve means disposed within the pressure tube below the subatmospheric pressure developing means, said valve means being responsive to the surface level sensing means for hermetically sealing the subatmospheric pressure developing means from the upper end of the holding means when the sample has reached a level therein to thereby maintain a subatmospheric pressure within said holding means and retain the sample in a quiescent state therein.

31. The system as in claim 29 further comprising means for calculating the weight concentration of the particles within the sample from the rate of change of the pressure within the holding means and from the height of the sample retained within the holding means above the upper surface of the aqueous medium.

32. A system for measuring the weight concentration of suspended particles within an aqueous medium comprising:
  hollow holding means for holding a column of the aqueous medium, said holding means having an upper end and an open lower end for placement into the aqueous medium;
  means for developing a subatmospheric pressure within the upper end of the holding means to thereby draw a sample of the aqueous medium into said holding means through the open lower end thereof to a location above an upper surface of said aqueous medium to thereby retain the sample in a quiescent state such that suspended particles within the sample gradually drop through the open lower end of the holding means by force of gravity;
  means for measuring the pressure over time within the holding means after the sample has been drawn thereinto to thereby develop a measurement of the rate of change of said pressure resulting from the settling of particles from the sample;
  means for determining the height of the sample retained within the holding means above the upper surface of the aqueous medium; and
  means for calculating the weight concentration of the particles within the sample from the rate of change of the pressure within the holding means and from the height of the sample retained within the holding means above the upper surface of the aqueous medium.

33. The system as in claim 32 further comprising:
  a pressure tube pneumatically connecting the subatmospheric pressure developing means to the upper end of the holding means;
  means disposed on the upper end of the holding means for sensing the surface level of the sample therein; and
  valve means disposed within the pressure tube below the subatmospheric pressure developing means, said valve means being responsive to the surface level sensing means for hermetically sealing the subatmospheric pressure developing means from the upper end of the holding means when the sample has reached a level therein to thereby maintain a subatmospheric pressure within said holding means and retain the sample in a quiescent state therein.

34. The system as in claim 32 further comprising means for calculating the settling velocity of the particles within the sample from the rate of change of the pressure within the holding means and from the height of the sample retained within the holding means above the upper surface of the aqueous medium.

35. A method of monitoring and controlling a feed rate of a flocculant into an aqueous medium having suspended particles therein comprising the following steps:
(a) placing an open lower end of a hollow holding means into the aqueous medium below an upper surface thereof;
(b) creating a subatmospheric pressure within an upper end of the holding means to thereby draw a sample of the aqueous medium into said holding means through the open lower end to a location above an upper surface of said aqueous medium;
(c) hermetically sealing the subatmospheric pressure developing means from the upper end of the holding means when the sample has reached a level therein to thereby maintain a subatmospheric pressure within said holding means and retain the sample in a quiescent state therein such that suspended particles within the sample gradually drop through the open lower end of the holding means by force of gravity;
(d) measuring the pressure over time within the holding means after the sample has been drawn thereinto to thereby develop a measurement of the rate of change of said pressure resulting from the settling of particles from the sample;
(e) determining the height of the sample retained within the holding means above the upper surface of the aqueous medium;
(f) calculating the settling velocity of the particles within the sample from the rate of change of the pressure within the holding means and from the height of the sample retained within the holding means above the upper surface of the aqueous medium; and
(g) selectively increasing the feed rate of the flocculant if the settling velocity is lower than a first value and decreasing the feed rate if the settling velocity is higher than a second value, to thereby achieve a desired settling velocity of the suspended particles corresponding to an optimal flocculant feed rate.

36. A method according to claim 35 wherein step (f) further comprises the following steps:
(h) calculating the weight concentration of the particles within the sample from at least one of the pressure measurements and the height of the sample retained within the holding means above the upper surface of the aqueous medium; and
(i) determining a desired settling velocity from the weight concentration of the particles within the sample.

37. A method according to claim 36 further comprising the following steps:
(j) determining the time required to draw the sample into the holding means;
(k) mathematically multiplying the time required to draw the sample by the settling velocity to thereby determine a theoretical quantity of particle free sample resulting from the settling of particles during the drawing of the sample into the holding means;
(l) calculating a corrected settling velocity from the theoretical quantity of particle free sample; and
(m) calculating a corrected weight concentration from the theoretical quantity of particle free sample.

38. A method according to claim 35 wherein step (a) further comprises the step of positioning the holding means to extend substantially vertically into the aqueous medium.

39. A method according to claim 35 wherein step (a) further comprises the step of positioning the holding means to extend into the aqueous medium at an inclined position to thereby increase the settling velocity of the particles within the sample and enable shorter intervals between pressure measurements.

* * * * *